(12) United States Patent
Gonnering

(10) Patent No.: US 7,235,071 B2
(45) Date of Patent: Jun. 26, 2007

(54) GAS-ASSISTED ELECTROSURGICAL ACCESSORY CONNECTOR AND METHOD WITH IMPROVED GAS SEALING AND BIASING FOR MAINTAINING A GAS TIGHT SEAL

(75) Inventor: Wayne J. Gonnering, Littleton, CO (US)

(73) Assignee: ConMed Corporation, Utica, NY (US)

( * ) Notice: Subject to any disclaimer, the term of this patent is extended or adjusted under 35 U.S.C. 154(b) by 367 days.

(21) Appl. No.: 10/789,509

(22) Filed: Feb. 27, 2004

(65) Prior Publication Data

US 2005/0192643 A1    Sep. 1, 2005

(51) Int. Cl.
*A61B 18/18*    (2006.01)
*A61M 1/00*    (2006.01)

(52) U.S. Cl. .............................. 606/41; 604/35; 606/48

(58) Field of Classification Search ............ 606/32–34, 606/38–41, 46, 48–50; 604/35
See application file for complete search history.

(56) References Cited

U.S. PATENT DOCUMENTS

| | | | |
|---|---|---|---|
| 4,781,175 A | | 11/1988 | McGreevy et al. |
| 4,901,719 A | * | 2/1990 | Trenconsky et al. .......... 606/49 |
| 4,936,842 A | | 6/1990 | D'Amelio et al. |
| RE34,780 E | | 11/1994 | Trenconsky et al. |
| 5,658,249 A | * | 8/1997 | Beland et al. ................. 604/33 |
| 5,836,909 A | * | 11/1998 | Cosmescu ..................... 604/35 |
| 5,888,198 A | | 3/1999 | Eggers et al. |
| 6,149,648 A | * | 11/2000 | Cosmescu ..................... 606/42 |
| 6,635,034 B1 | | 10/2003 | Cosmescu |

OTHER PUBLICATIONS

PCT International Search Report, dated May 12, 2005.
Written Opinion of the International Searching Authority, dated May 12, 2005.

* cited by examiner

*Primary Examiner*—Michael Peffley
(74) *Attorney, Agent, or Firm*—John R. Ley

(57) ABSTRACT

Male and female mating pieces of a gas-assisted electrosurgical accessory connector are connectable together by radially contacting a sealing surface formed on one mating piece with a resilient radially-compressible sealing member carried on the other mating piece. A gas-tight seal exists along a length of the sealing surface as the two mating pieces connect with relative connection movement. The existence of the gas-tight seal over a range of relative connection movement maintains the seal if the mating pieces should become slightly disconnected. The mating pieces are also restrained against separation from one another. A recess is formed in one of the mating pieces and a retention member carried on the other one of the mating pieces is biased into contact with the recess. Separation of the two connected members requires manual force to extract the retention member from the recess. The amount of manual force required is greater than that normally experienced from movement during use, thereby inhibiting unintentional separation.

35 Claims, 13 Drawing Sheets

GAS-ASSISTED ELECTROSURGICAL ACCESSORY CONNECTOR AND METHOD WITH IMPROVED GAS SEALING AND BIASING FOR MAINTAINING A GAS TIGHT SEAL

This invention relates to gas-assisted electrosurgery, and more particularly to a new and improved accessory connector for connecting a gas-assisted electrosurgical accessory to a gas-assisted electrosurgical unit which includes an electrosurgical generator and a gas delivery apparatus. The accessory connector is less susceptible to gas leaks, is more resistant to unintentional disconnection or separation of internal gas sealing surfaces, and is backwards compatible with certain previous gas-assisted electrosurgical accessory connectors, among other improvements.

BACKGROUND OF THE INVENTION

Electrosurgery involves the application of radio-frequency (RF) electrical energy to cut a patient's tissue, to coagulate blood flow from the tissue, or to both cut and coagulate simultaneously. An electrosurgical generator creates the RF electrical energy, and the RF energy is applied to the tissue by an applicator or pencil-like handpiece which is manipulated by a surgeon to cut and coagulate. Gas-assisted electrosurgery additionally involves conducting the RF energy to the tissue in a stream of ionized conductive gas. The gas stream clears blood and other fluids from the surface of the tissue, thereby allowing the RF energy to interact directly with the tissue without the fluid diverting all or part of the electrical energy away from the tissue. The transfer of the RF energy through the ionized gas stream directly to the tissue without diversion from fluid achieves an enhanced electrosurgical effect. U.S. Pat. No. 4,781,175 and Re U.S. Pat. No. 34,780 are exemplary of gas-assisted electrosurgery apparatus. Both of these U.S. patents are assigned to the same assignee as the present application.

A nozzle at the distal end of the handpiece shapes the gas into a flow stream of desired characteristics. An electrode is positioned within the nozzle to ionize the gas and to transfer the RF energy into conductive pathways within the gas stream. An accessory hose conducts the gas flow from a gas delivery apparatus to the nozzle, and an accessory conductor conducts the RF energy from an electrosurgical generator to the electrode within the nozzle. The accessory hose and conductor and the nozzle and electrode are part of the gas-assisted electrosurgical accessory.

An accessory connector connects the accessory hose and conductor to a housing of a gas-assisted electrosurgical unit, which includes the electrosurgical generator and gas delivery apparatus. The accessory connector permits different gas-assisted electrosurgical accessories to be used and replaced as necessary or desirable. One mating piece of the accessory connector is connected to the accessory handpiece, and another complementary mating piece of the accessory connector is connected to the housing of the gas-assisted electrosurgical unit. The accessory connector transfers the gas flow and RF energy from the gas-assisted electrosurgical unit into the accessory hose and onto the accessory conductor of the accessory.

In some gas-assisted electrosurgery accessories, such as probes used in gastrointestinal electrosurgical applications, the pencil-like handpiece and the cord are either not used or they are considerably modified in form. For example, in a gas-assisted gastrointestinal electrosurgical probe, the accessory hose takes the form of a small diameter gas-conducting tube that extends directly from the accessory connector to the end of the gas-conducting tube where the nozzle is located. The accessory conductor extends within the gas conducting tube. No pencil-like handpiece exists, because the end of the gas-conducting tube with the nozzle and the internal electrode is manipulated by an endoscope or a laparoscope into which the probes inserted. A gastrointestinal probe of this type is an example of a gas-assisted electrosurgery accessory used to perform minimally invasive electrosurgical procedures. A variety of other types of accessories using handpieces and different lengths of cords and different configurations of nozzles are available to perform other open types of electrosurgical procedures.

The accessory connector should transfer the gas flow and the RF electrical energy without leakage to the ambient environment. In a typical gas-assisted electrosurgical procedure, the surgeon selects a desired gas flow and a desired amount of electrosurgical energy to be applied to the tissue. In many cases, the amount of gas flow and the amount of the electrical energy are coordinated to achieve a desired electrosurgical effect. If gas leaks from the accessory connector, the desired amount of gas will not be delivered from the nozzle, and the desired electrosurgical effect may not be achieved. Similarly, if current leakage or conduction of some of the RF energy occurs at the accessory connector, the desired electrosurgical effect may not be achieved. RF energy leakage at the accessory connector or any other location along the cord or within the handpiece, can cause an unintended burn to the surgeon, operating room personnel or the patient, or may damaged the electrosurgical generator.

An example of a gas-assisted electrosurgery accessory connector is described in U.S. Pat. No. Re 34,780. The gas sealing capability of the accessory connector described in this U.S. patent is achieved by an axial contact seal. The gas-confining integrity of such a seal depends upon the two mating pieces of the accessory connector remaining in an axially forced-together relationship. Such a relationship is achieved by screwing together the complementary threads of the two mating pieces until the two sealing surfaces axially contact one another. While this threaded-together relationship provides an effective gas-tight axial contact seal in most circumstances, it is possible for the threaded connection of the two mating pieces to loosen over the relatively lengthy duration of many surgical procedures due to the continual movement of the cord and the handpiece. It is not unusual for the threaded connection to loosen if the cord is accidentally stepped on, pulled or bumped by operating room personnel while performing the surgical procedure. Loosening of the two connected mating pieces of the accessory connector, even to a small degree, is likely to cause the sealing surfaces of the accessory connector to separate slightly, resulting in a leak gas.

The surgeon and the operating room personnel are not likely to recognize a leak at the accessory connector. The surgeon's attention is focused almost exclusively on creating the desired affects at the surgical site. The surgeon depends almost exclusively on the operating room personnel to supply the necessary equipment for use when the surgeon needs that equipment. In addition to serving the needs of the surgeon, the operating room personnel are focused on many other responsibilities associated with the surgical procedure, such looking after and monitoring as the welfare of the patient. The tissues encountered during a typical electrosurgical procedure vary substantially in electrical impedance and vascularity, both of which have a significant impact on the electrosurgical effect achieved. Since the surgeon expects variations in the surgical effect due to tissue differences, the surgeon may not recognize that the performance of the gas-assisted electrosurgical unit may have become compromised as a result of a gas leak at the accessory connector, resulting from continual movement of the cord and the handpiece during the procedure or from the cord having been accidentally stepped on, pulled or bumped during the surgical procedure.

The problems of gas leaks at the accessory connector may be aggravated with gas-assisted gastrointestinal electrosurgical probes. A relatively small diameter gas-conducting tube is required for insertion into an instrument channel of the endoscope or laparoscope. The endoscope or laparoscope must be relatively narrow to permit it to be inserted within a lengthy hollow organ in the gastrointestinal tract or to be inserted within an inflated body cavity. The gas flow rate through the relatively small diameter gas-conducting tube is less, causing the effect of a relatively small leak to magnify the extent of deviation of the gas flow from the nozzle, thereby impacting the expected performance.

These and other considerations have led to the improvements of the present invention.

SUMMARY OF THE INVENTION

In general, the present invention pertains to a new and improved gas-assisted electrosurgery accessory connector which does not depend on an axial contact seal for confining gas flow within the accessory connector. Instead, the improved accessory connector of the present invention uses a radial compression seal. The radial compression seal maintains a leak-free seal even if the two mating pieces of the accessory connector become somewhat loosened during the course of a surgical procedure. In addition, the new and improved accessory connector biases the two mating pieces of the accessory connector into a fully connected relationship to resist unintentional loosening of the two mating pieces. These and other improvements are achieved in a manner which permits backward-compatible use of certain pre-existing accessory connectors of the type described in U.S. Pat. No. Re 34,780. The backwards compatibility allows the improvements of the present invention to be incorporated in the mating piece of the accessory connector which is connected to the housing of the gas-assisted electrosurgical unit, so that existing previous accessories can be used. Furthermore, improvements in the mating piece of the accessory connector which is attached to the accessory does not prohibit the use of that accessory with the complementary mating piece of the previous form of the accessory connector. Thus, the improvements in both mating pieces of the present accessory connector may be used with the previous forms of the complementary mating pieces unknown gas-assisted accessory connectors, without the necessity to change the mating piece attached to the housing of the gas-assisted electrosurgical unit and without the necessity to purchased new accessories.

In accordance with these and other improvements, the new and improved gas-assisted electrosurgical accessory connector is formed by two mating pieces which are connectable to one another with a relative connection movement along an axis toward one another. A sealing surface is formed on one mating piece, and the sealing surface extends generally parallel with the axis for a distance along the axis. A resilient radial sealing member is carried on the other mating piece at a location which contacts and seals against the sealing surface with radial force upon the two mating pieces connecting with relative connection movement.

Other preferable aspects of the improved accessory connector include extending the sealing surface parallel to the axis over a predetermined length to permit the sealing member to contact and seal against the sealing surface over a range of relative connection movement of the two mating pieces. The sealing member is an annularly shaped resilient O-ring which is radially compressed to establish a gas-tight seal for confining a gas flow from the gas-assisted electrosurgical unit through the connected mating pieces to the accessory connector.

Another aspect of the improved accessory connector includes a retention mechanism operative between the connected mating pieces. The retention mechanism restrains the connected mating pieces against separation from one another. Preferably, the retention mechanism comprises a recess formed on one of the mating pieces and a retention member carried on the other one of the mating pieces. The retention member moves into the recess upon the two mating pieces connecting with relative connection movement, and the retention member moves out of the recess with manual force applied between the mating pieces to separate them from one another.

Still another aspect of the present invention includes a method of connecting together two mating pieces of a gas-assisted electrosurgical accessory. The method comprises connecting the two mating pieces by moving the two mating pieces together along an axis in a relative connection movement, contacting a sealing member carried on one mating piece with a sealing surface formed the other mating piece and which extends generally parallel with the axis for a distance along the axis, and resiliently compressing the sealing member in a radial direction relative to the axis in contact with the sealing surface to establish a gas tight seal over a range of the relative connection movement.

Preferably the method involves conducting a gas flow and RF electrical energy between the connected two mating pieces, contacting and sealing the sealing member with the sealing surface over a range of relative connection movement of the two mating pieces over a portion of the predetermined length of the sealing surface, and conducting the gas flow and the RF electrical energy in a space circumscribed by the sealing surface and the contact of the sealing member with the sealing surface.

Another aspect of the method of the present invention involves restraining the connected mating pieces against separation. Preferably the restraint is accomplished by moving a retention member carried by one mating piece into a recess formed the other mating piece upon the two mating pieces connecting with relative connection movement, and moving the retention member out of the recess with manual force applied between the two connected mating pieces to separate the mating pieces from one another.

A more complete appreciation of the scope of the present invention and the manner in which it achieves the above-noted and other improvements can be obtained by reference to the following detailed description of presently preferred embodiments taken in connection with the accompanying drawings, which are briefly summarized below, and by reference to the appended claims.

DETAILED DESCRIPTION

Figure 1:
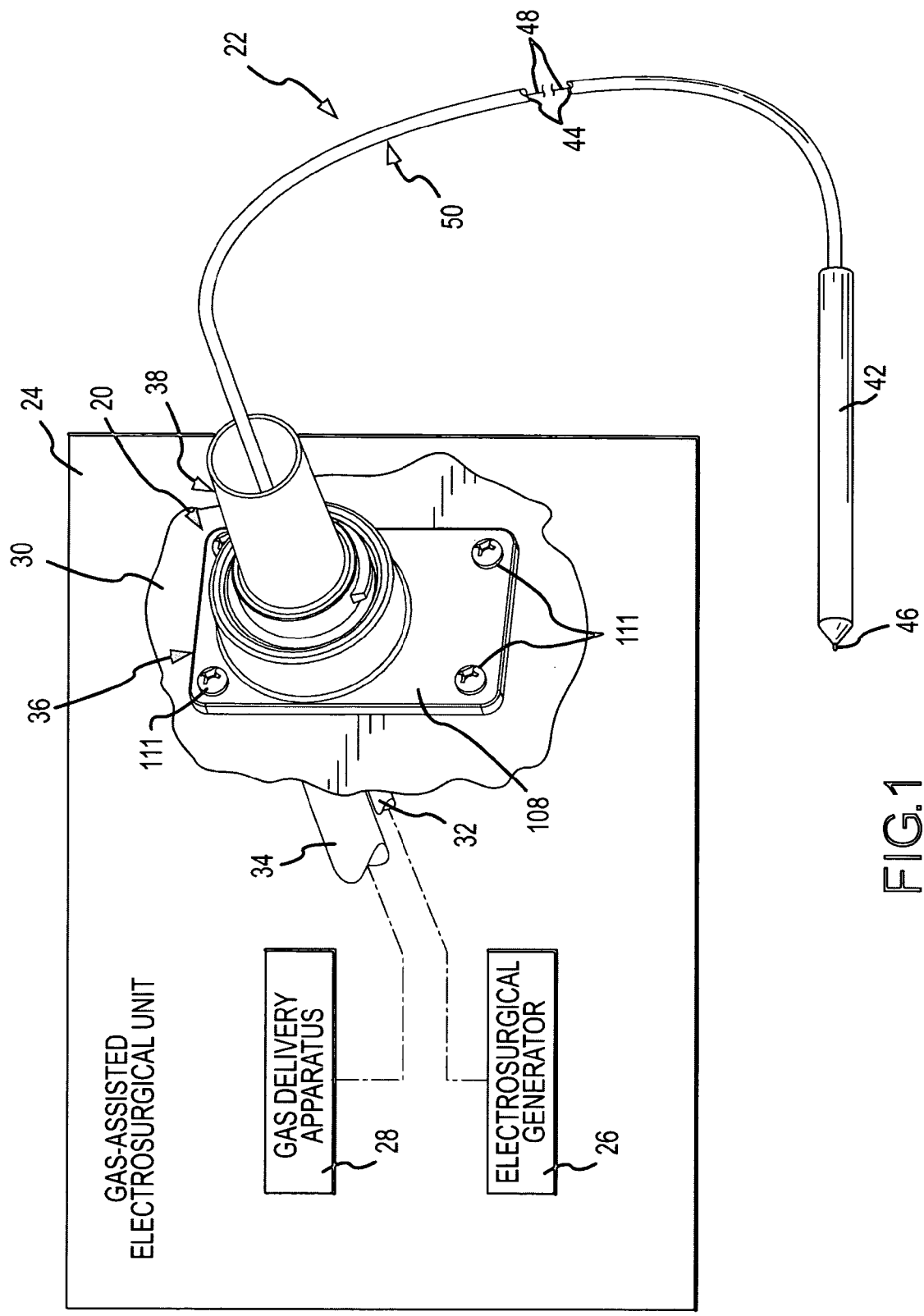
FIG. 1 is a perspective view of a gas-assisted electrosurgical accessory connector, a gas-assisted electrosurgical accessory, and a broken-away portion of a gas-assisted electrosurgical unit otherwise shown primarily in block diagram form.
Figure 2:
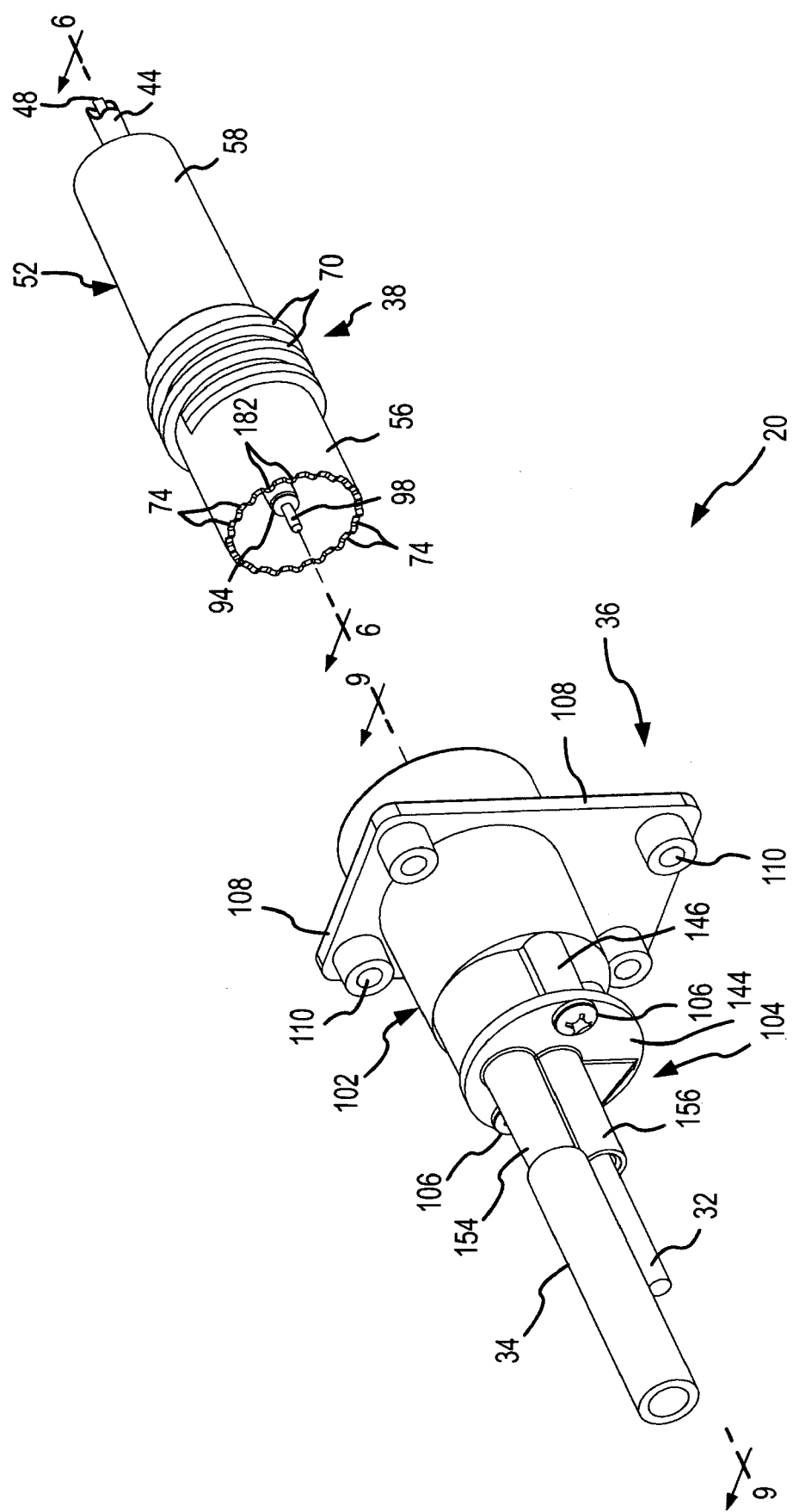
FIG. 2 is an exploded perspective view of the accessory connector shown in FIG. 1, with female and male mating pieces separated from one another and shown from a rear perspective compared to the front perspective of the accessory connector shown in FIG. 1.

An accessory connector 20 incorporating the present invention is shown in FIGS. 1 and 2. The accessory connector 20 connects a gas-assisted electrosurgical accessory 22 to a conventional gas-assisted electrosurgical unit 24. The gas-assisted electrosurgical unit 24 includes a conventional electrosurgical generator 26 and a conventional gas delivery apparatus 28, both of which are typically contained wholly or partially within a housing 30 (partially shown) of the gas-assisted electrosurgical unit 24. The electrosurgical generator 26 generates radio frequency (RF) electrical energy of preselected characteristics from conventional alternating current power, and applies the RF electrical energy on a supply conductor 32 within the housing 30. The gas delivery apparatus 28 includes a source of preferably-inert and ionizable gas (not shown), from which a flow of gas of preselected and controlled characteristics is derived and supplied within the housing 30 through a supply conduit 34.

A female mating piece 36 of the accessory connector 20 is connected to receive the RF energy from the supply conductor 32 and the gas flow from the supply conduit 34. A male mating piece 38 of the accessory connector 20 connects with the female mating piece 36 to receive the RF energy and the gas flow transferred from the female mating piece 36. The male mating piece 38 conducts the RF energy and gas flow to the electrosurgical accessory 22. The accessory 22 is connected to the electrosurgical unit 24 by the connection of the mating pieces 36 and 38. Preferably, the male mating piece 36 forms a part of the accessory 22.

In the form shown in FIG. 1, the accessory 22 includes a pencil-like applicator or handpiece 42 connected to one end of a flexible gas-conducting accessory hose 44. The handpiece 42 also includes a nozzle 46 from which a flow of gas issues. The gas flow from the male mating piece 38 is conducted through the hose 44 and into the handpiece 42 and out of the nozzle 46. The characteristics of the nozzle 46 shape the gas flow into a desired flow stream (not shown) which is applied to the patient's tissue (not shown). An electrode (not shown) is located within the nozzle 46. The electrode within the nozzle 46 is connected to an accessory electrical conductor 48 which, in the form of the accessory shown in FIG. 1, is located within the accessory hose 44. The accessory conductor 48 conducts the RF energy from the male mating piece 38 to the electrode within the nozzle 46. The RF energy applied to the electrode within the nozzle 46 ionizes the gas flowing through the nozzle 46 and is transferred to the patient's tissue in ionized conducted pathways within the flow stream of gas issuing from the nozzle 46, to create the desired electrosurgical effect.

In the form of the gas-assisted electrosurgical accessory 22 shown in FIG. 1, the accessory hose 44 and the internal accessory conductor 48 constitute a cord 50 which connects the handpiece 42 to the accessory connector 20. The length of the cord 50 many vary according to type of accessory 22. Not all gas-assisted electrosurgical accessories 22 include the handpiece 42. For example, a gas-assisted gastrointestinal electrosurgical probe utilizes only a flexible gas-conducting tube or supply hose which terminates at a nozzle. The supply hose fits within an endoscope or a laparoscope, and the surgeon manipulates the position of the nozzle end of the hose by manipulating the endoscope or the laparoscope within a hollow organ or within an expanded body cavity of the patient.

The accessory connector 20 transfers the gas from the gas-assisted electrosurgical unit 24 to the accessory 22 in a manner which significantly improves its ability to avoid and prevent gas leaks. The accessory connector 20 also offers a significantly improved ability to resist accidental loosening and separation of the mating pieces 36 and 38, to further avoid gas leaks. The accessory connector 20 conducts the RF energy from the electrosurgical unit 24 to the accessory 22 in a manner which does not divert, leak or short-circuit the RF energy to the housing 30 or to the surrounding ambient environment. The configuration of each mating piece 36 and 38 allows each mating piece to be connected to and used in a backward compatible manner with the pre-existing complementary mating pieces of pre-existing gas-assisted electrosurgical accessories 22. These and other advantages and improvements will become more apparent from the details of the accessory connector 20, described below.

Figure 3:
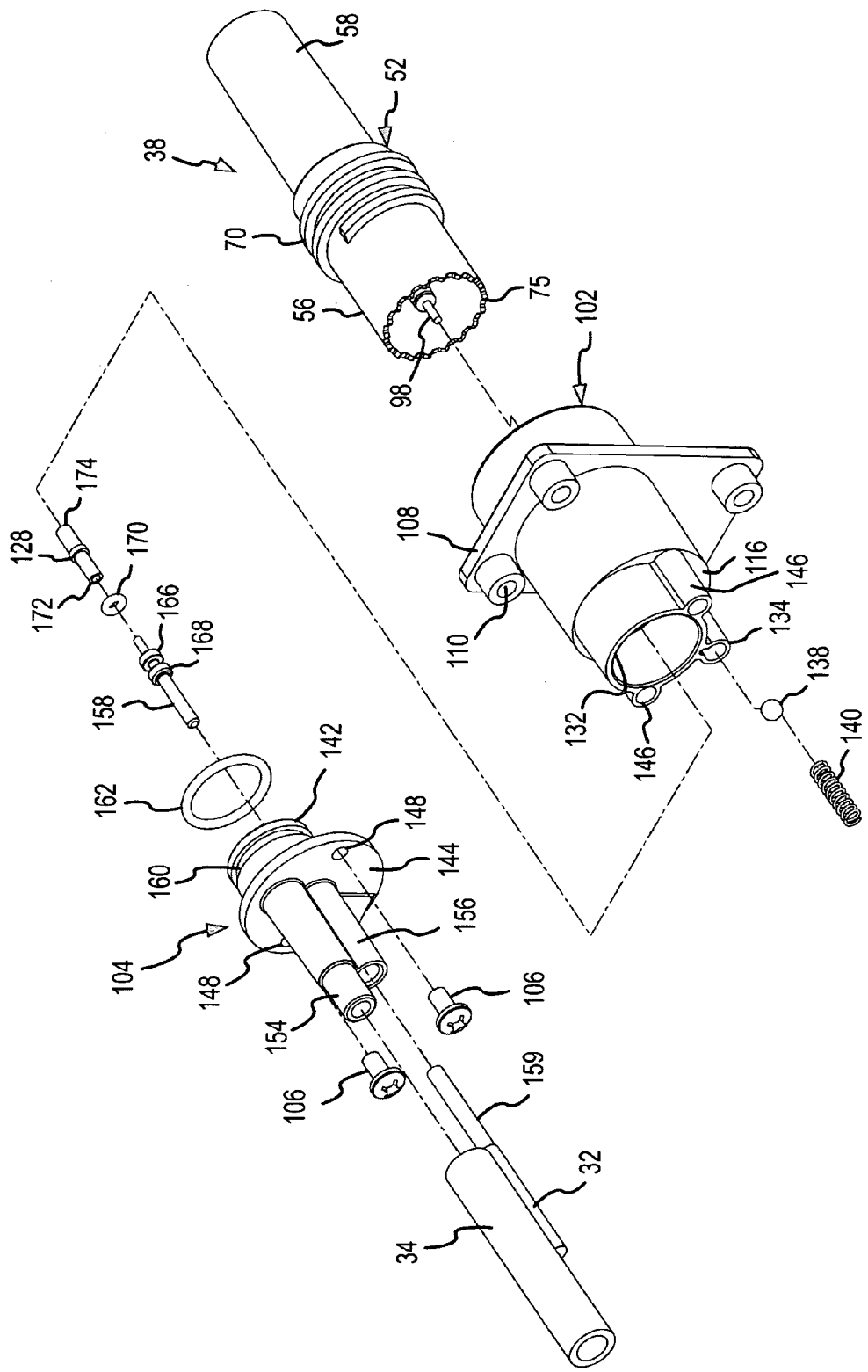
FIG. 3 is a perspective view of the female and male mating pieces of the accessory connector shown in FIG. 2, shown separated from one another and with the components of the female mating piece exploded.
Figure 4:
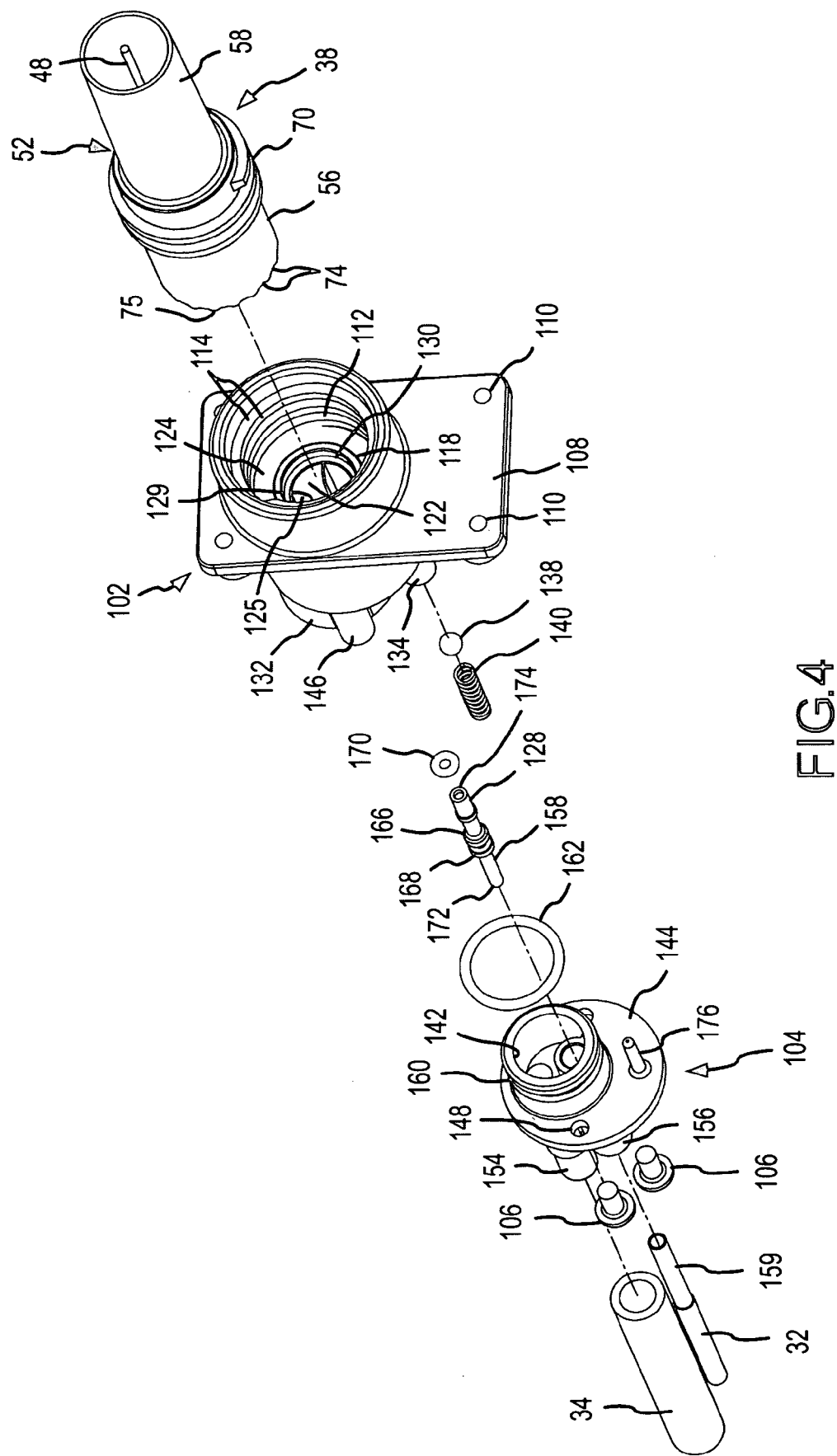
FIG. 4 is a perspective view similar to FIG. 3, shown from a front perspective compared to the rear perspective view shown in FIG. 3.
Figure 5:
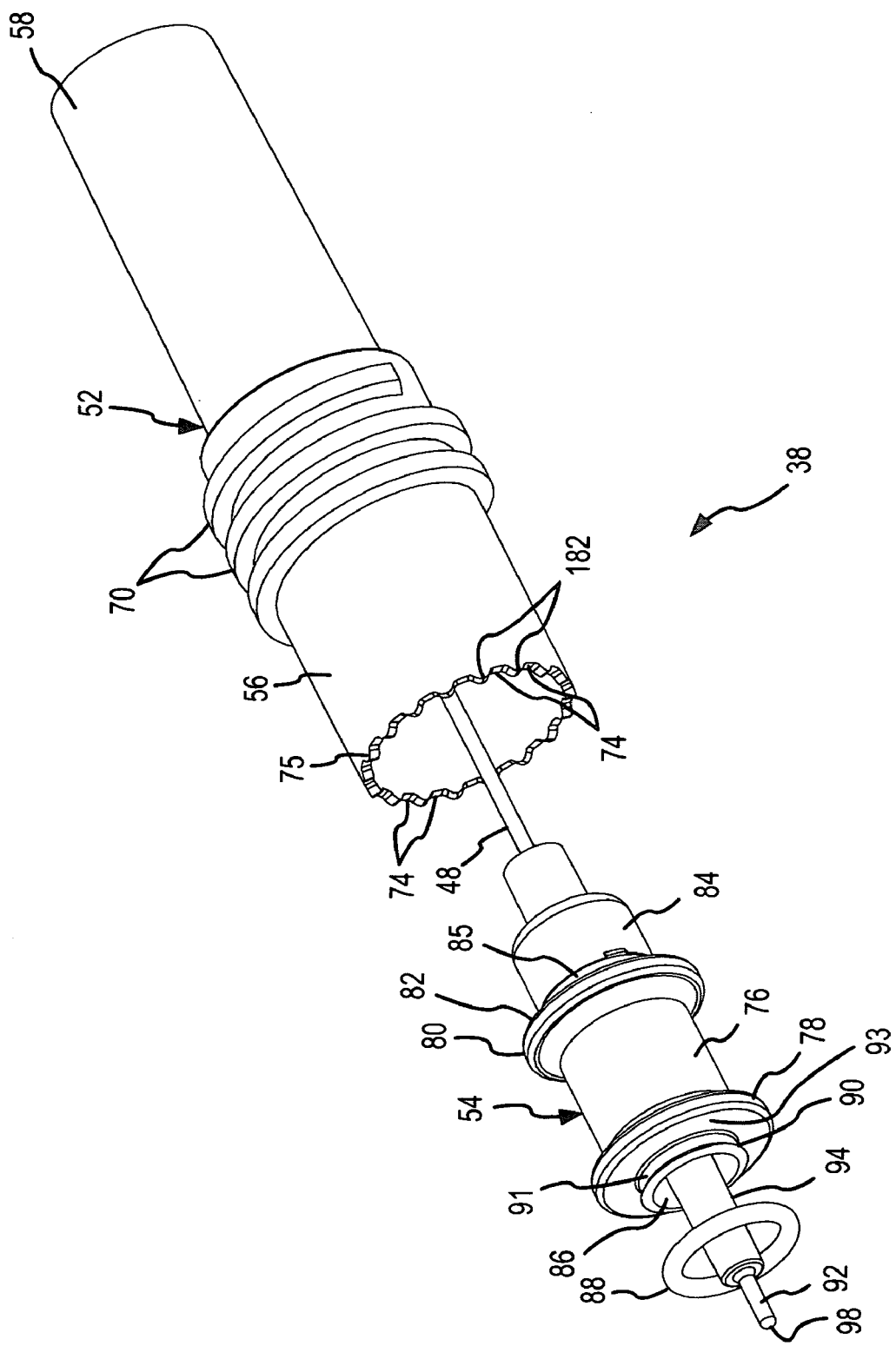
FIG. 5 is an exploded perspective view of the male mating piece of the accessory connector shown in FIGS. 1-4.
Figure 6:
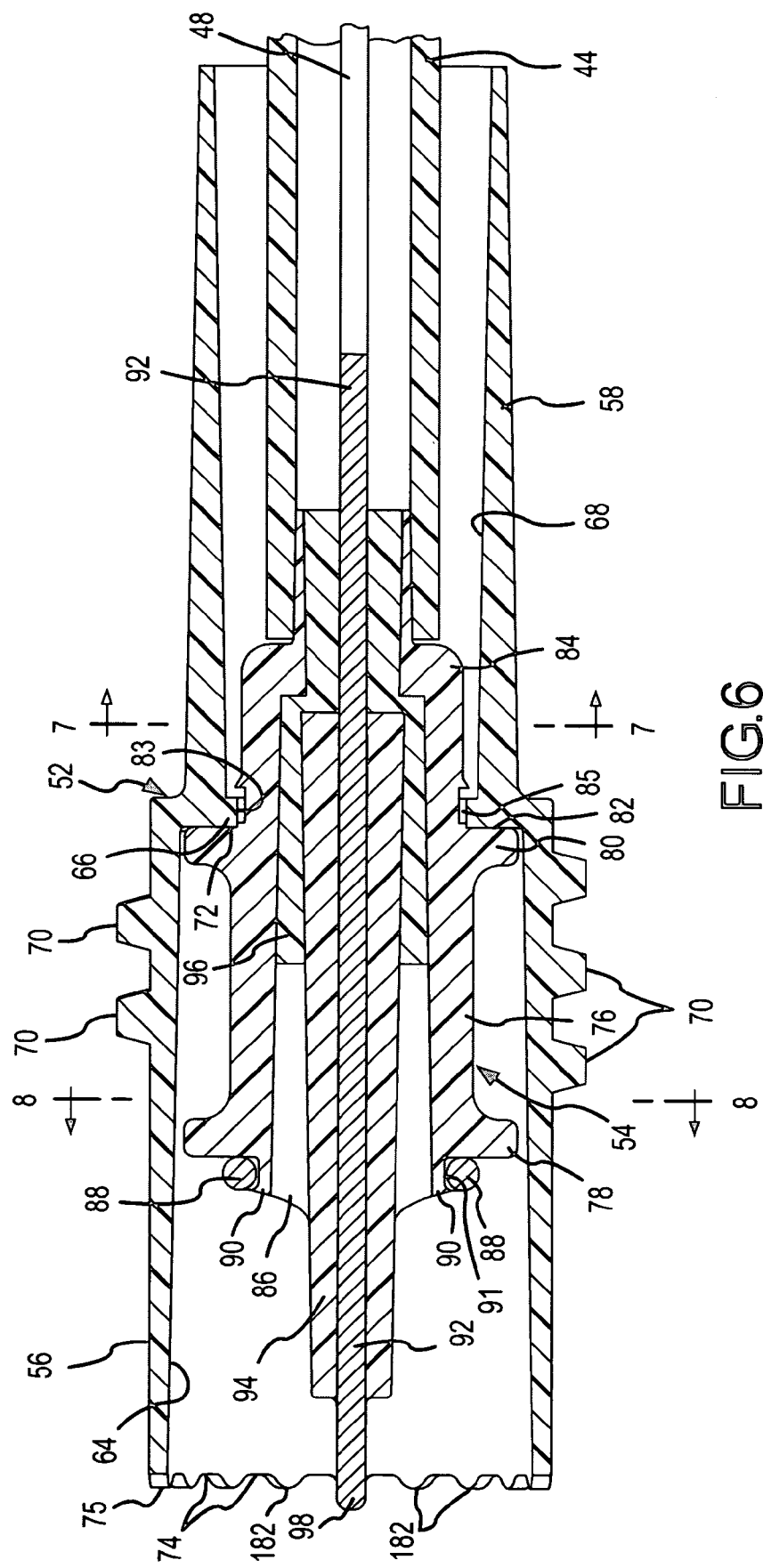
FIG. 6 is an axial cross-sectional view along an axis of the male mating piece of the accessory connector shown in FIGS. 1-5, taken substantially in the plane of line 6-6 in FIG. 2.
Figure 13:
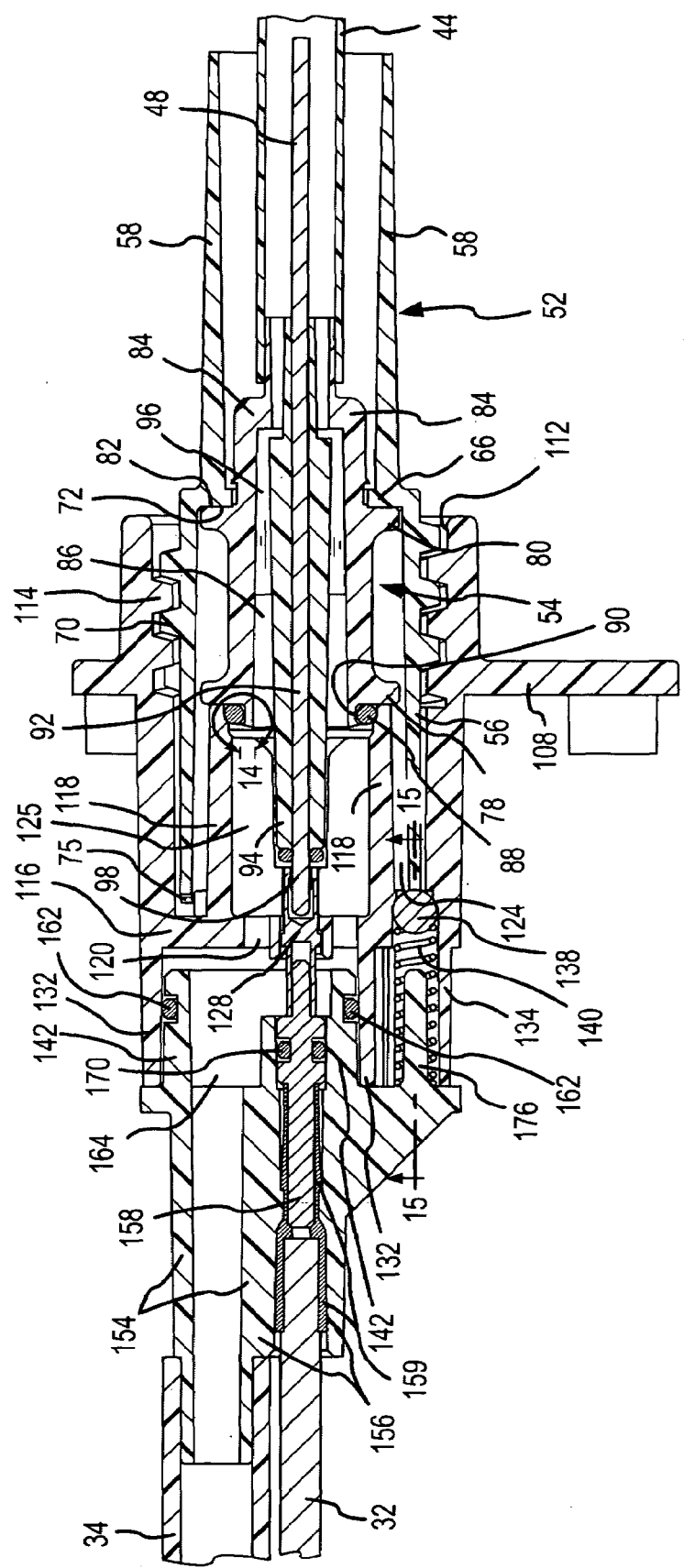
FIG. 13 is an axial cross-sectional view of connected female and male mating pieces, similar to a combination of FIGS. 6 and 9, taken substantially in a vertical plane through an axis of the accessory connector shown in FIG. 1.

Details of the male mating piece 38 of the connector 20 are shown generally in FIGS. 1-4 and more specifically in FIGS. 5-8. The male mating piece 38 of the connector 20 is essentially the same as a previous prior art configuration of a gas-assisted accessory connector, with the exception of certain detents 74 described below. As shown in FIGS. 5 and 6, the male mating piece 38 includes an external hollow sleeve member 52 within which there is positioned an interior hub member 54. In general, the sleeve member 52 connects the male mating piece 38 to the female mating piece 36 (as shown in FIG. 13), and positions the hub member 54 to receive the gas flow and RF energy from the female mating piece 36. The accessory hose 44 and the accessory conductor 48 are connected to the hub member 54 to transfer the gas flow and the RF energy to the handpiece 42.

The sleeve member 52 has a relatively larger-diameter generally-cylindrical end portion 56 and a relatively smaller-diameter generally-cylindrical end portion 58. The larger end portion 56 and the smaller end portion 58 are respectively located on a front or forward end and a rear or rearward end of both the sleeve member 52 and the male mating piece 38. An interior sidewall 64 of the larger end portion 56 tapers with a slightly decreasing radius from the front end to a radially-extending abutment shoulder 66. An interior sidewall 68 of the smaller end portion 58 tapers with a slightly decreasing radius from the rear end to the abutment shoulder 66. The abutment shoulder 66 is located near the axial center of the hollow interior of the sleeve member 52, and the larger end portion 56 transitions to the smaller end portion 58 at approximately the location of the abutment shoulder 66.

The exterior surface of the larger end portion 56 includes threads 70 which project outwardly from a location starting approximately midway along the length of the larger end portion 56 and terminating approximately adjacent to the abutment shoulder 66. The threads 70 are used to connect the male mating piece 38 to the female mating piece 36, by screwing the threads 70 into complementary threads (114, FIGS. 9 and 13) of the female mating piece. The smaller end portion 58 is used as a handle or grip to rotate the sleeve member 52 when screwing it into the female mating piece 36. The smaller end portion 58 extends from the female mating piece 36, thereby enabling the smaller end portion 58 to be gripped when rotating the sleeve member 52 to connect or disconnect the male mating piece 38 from the female mating piece 36.

The abutment shoulder 66 includes a forward-facing contact surface 72 that contacts the rear end of the hub member 54 when the sleeve member 52 is advanced into the female mating piece 38 during connection of the two mating pieces 36 and 38. The advancement of the sleeve member 52 and the abutment shoulder 66 forces the hub member 54 forward into operative contact with components of the female mating piece.

A series of circumferentially spaced detents 74 are formed in a forwardmost edge 75 of the larger end portion 56. The detents 74 are indentions or recesses which are indented rearwardly from the forwardmost locations along the forward edge 75. The detents 74 are used in the manner described below to assist in maintaining the sleeve member 52 in a position restrained from unintentional loosening or unscrewing from the female mating piece 36. With the exception of the detents 74, the configuration of the male mating piece 38 is essentially the same as a prior art configuration. The prior art male mating piece has a smooth cylindrical forward edge, without the series of circumferentially spaced detents 74.

The hub member 54 includes a hollow spool-like body portion 76 having a front annular ridge 78 and a rear annular ridge 80. The forward-facing contact surface 72 of the abutment shoulder 66 contacts a rearward-facing contact surface 82 of the rear annular ridge 80. Force from the sleeve member 52 is transferred to the hub member 54 through the contact of the two surfaces 72 and 82. The surfaces 72 and 82 are relatively smooth, thereby permitting the forward-facing contact surface 72 to rotate relative to the stationary rearward-facing contact surface 82, while the sleeve member 52 rotates relative to the hub member 54 when connecting the mating pieces 36 and 38 (FIG. 13). The annular ridges 78 and 80 align the hub member 54 relative to the interior surface 64 of the larger end portion 56 to keep the hub member 54 generally centered within the hollow interior of the sleeve member 52 to facilitate connecting the mating pieces 36 and 38.

A hollow stub portion 84 extends integrally from the rear of the spool-like body portion 76. The hub member 54 is retained relative to the sleeve member 52 by the slight radial extension of a radially inward-facing edge 83 of the abutment shoulder 66 into a slight annular recess 85 formed into the hub member 54 between the spool-like body portion 76 and the stub portion 84. The radially inward facing edge 83 of the abutment shoulder 66 extends into the recess 85 only a very slight amount, thereby allowing the hub member 54 to be snapped into the retained position within the sleeve member 52. There is sufficient clearance between the edge 83 and the recess 85 to avoid interference when the sleeve member 52 is rotated relative to the hub member 54 during connection of the mating pieces 36 and 38.

A gas passageway 86 is defined through the center of the hollow spool-like body portion 76 and the hollow stub portion 84. The gas passageway 86 extends from the forward end of the hollow spool-like body portion 76 to the rear end of the stub portion 84. The accessory hose 44 is connected to the rear end of the stub portion 84. The inside surface of the smaller end portion 58 has a larger diameter than the stub portion 84 and the accessory hose 44 to permit the hose 44 to be connected to the hub member 54 within the interior of the smaller end portion 58. The gas flow transferred from the female mating piece 36 enters the gas passageway 86 at the forward end of the spool-like body portion 76, flows through the hollow interior of the hub member 54, and enters the accessory hose 44 at the rear end of the stub portion 84.

The gas flow transferred from the female mating piece 36 is confined within the gas passageway 86 by an O-ring seal 88 located at the forward end of the hub member 54. The O-ring 88 surrounds the gas passageway 86 and creates the seal between the forward end of the hub member 54 and the adjoining outward portions of the female mating piece 36. A relatively short sleeve-like extension 90 extends forward from the front end of the spool-like body portion 76 outside of the gas passageway 86. An annular groove 91 is formed in the extension 90. The O-ring 88 is placed over the sleeve-like extension 90 and is seated within the annular groove 91. The O-ring 88 is expanded slightly when placed over the extension 90, and the force created by the slight expansion of the resilient material of the O-ring 88 maintains the O-ring 88 within the annular groove 91 during connection and disconnection of the mating pieces 36 and 38. A forward-facing surface 93 extends radially outward from the sleeve-like extension 90 at a position to the rear of the annular groove 91. The surface 93 extends from the sleeve-like extension 90 radially outward to the radially outer edge of the forward annular ridge 78.

Figure 7:
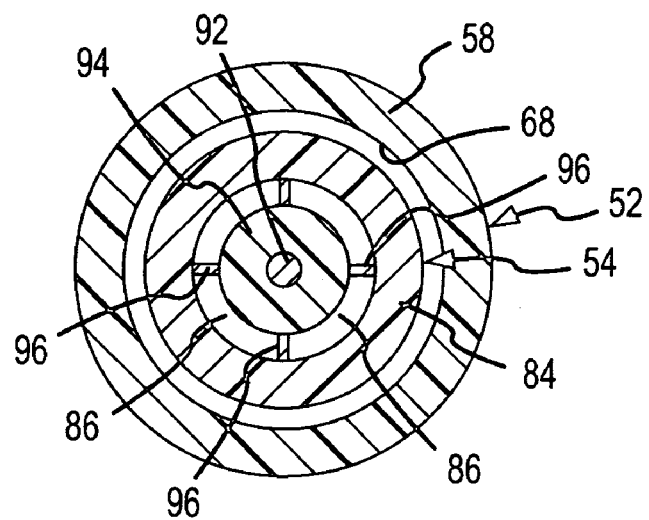
FIG. 7 is a transverse cross-sectional view taken substantially in the plane of line 7-7 of FIG. 6.
Figure 8:
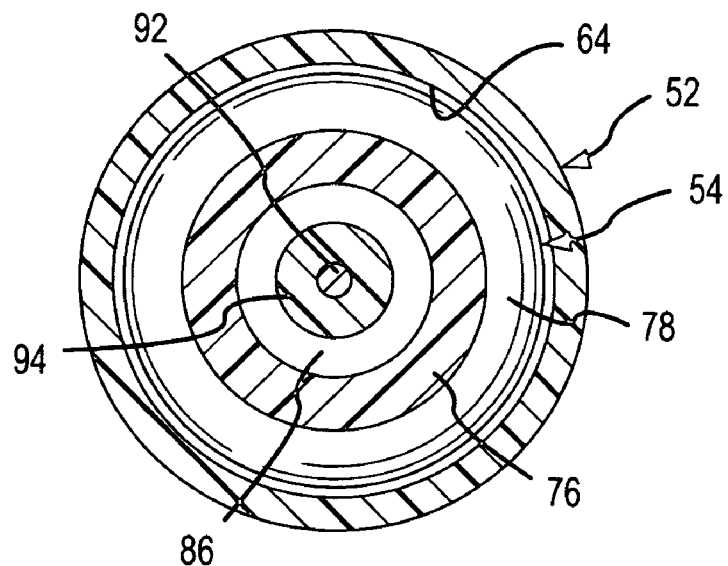
FIG. 8 is a transverse cross-sectional view taken substantially in the plane of line 8-8 of FIG. 6.

A metallic connector electrode 92 extends through the hollow center of the spool-like body portion 76 within the gas passageway 86. A rear end of the connector electrode 92 is connected to the accessory conductor 48 located within the accessory hose 44. The connection between the accessory conductor 48 and the connector electrode 92 is conventional, such as by swaging or soldering. The connector electrode 92 is surrounded by an insulating sleeve 94 within the hollow interior of the spool-like body portion 76. The insulating sleeve 94 is an integral part of the spool-like body portion 76. As shown in FIG. 7, the insulating sleeve 94 is held in the center position within the hollow interior of the spool-like body portion 76 by ribs 96 which extend radially within the hollow interior of the spool-like body portion 76 between the body portion 76 and the sleeve 94. The ribs 96 are oriented parallel to the gas flow through the gas passageway 86, and therefore do not restrict or block the gas flow in the open spaces between the ribs 96 within the passageway 86. The ribs 96 extend to the spool-like body portion 76 only from the rear portion of the insulating sleeve 94. The front portion of the sleeve 94 extends in a cantilevered manner, as shown in FIG. 8. The ribs 96 retain the insulating sleeve 94 in a fixed position within the gas passageway 86. The connector electrode 92 is inserted into the insulating sleeve 94 and is retained in a fixed position within the insulating sleeve 94, preferably by insert molding. Retained in this manner, the connector electrode 92 is maintained in an centered position at the axis of the male mating piece 38.

The insulating sleeve 94 terminates before reaching the forward end of the connector electrode 92, thereby exposing a forward end 98 of the connector electrode 92. The exposed forward end 98 permits the connector electrode 92 to make electrical contact with an electrical socket (128, FIGS. 9 and 13) of the female mating piece 36 to transfer the RF electrical energy from the gas-assisted electrosurgical unit 24 to the accessory 22 (FIG. 1).

Details of the female mating piece 36 of the accessory connector 20 are shown generally in FIGS. 1–4 and more specifically in FIGS. 3, 4 and 9–12. The improvements of the present invention reside primarily, but not exclusively, in the female mating piece 36. The female mating piece 36 includes a receptacle housing 102 to which a tailpiece 104 is attached by screws 106. The receptacle housing 102 and the tailpiece 104 are formed of a dielectric insulating material. A flange 108 extends outward from the housing body 102, and holes 110 in the flange 108 receive screws 111 or other fasteners to attach the female mating piece 36 to the housing 30 of the gas-assisted electrosurgical unit 24 (FIG. 1).

The receptacle housing 102 defines an outward-opening receptacle 112 at an outer end of the female mating piece 36. The forward portion of the male mating piece 38, including approximately all of the larger cylindrical end portion 56 of the sleeve member 52 and the components within the larger end portion 56 (FIG. 6), are inserted into the receptacle 112 when the mating pieces 36 and 38 are connected (FIG. 13). An outer end of the tailpiece 104 connects to the inner end of the receptacle housing 102. The supply conductor 32 from the electrosurgical generator 26 (FIG. 1) and the supply conduit 34 from the gas delivery apparatus 28 (FIG. 1), are connected to an inner end of the tailpiece 104. The tailpiece 104 delivers the gas and the RF energy to the female mating piece 36.

Figure 10:
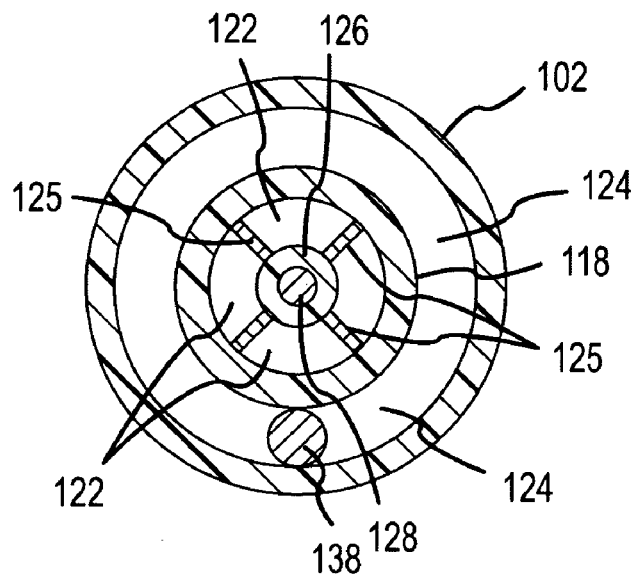
FIG. 10 is a transverse cross-sectional view taken substantially in the plane of line 10-10 of FIG. 9.

Internal threads 114 of the receptacle housing 102 surround the outer end of the receptacle 112 to mesh with the external threads 70 on the larger cylindrical end portion 56 (FIGS. 5 and 6) of the sleeve member 52 of the male mating piece 38 when the mating pieces 36 and 38 are connected (FIG. 13). The receptacle 112 continues inwardly from the inner termination point of the internal threads 114 to an intermediate wall 116 which extends transversely across the receptacle 112 at a location between the outer and inner ends of the receptacle housing 102. A hollow cylindrical sleeve 118 is attached to the intermediate wall 116 and projects outwardly from the intermediate wall 116 into the receptacle 112. An opening 120 is formed through the intermediate wall 116 in alignment with an elongated hollow interior 122 of the hollow sleeve 118, as shown in FIG. 10. Gas flow from the tailpiece 104 is conducted through the opening 120 and into the interior 122 of the sleeve 118.

The hollow sleeve 118 extends outwardly from the intermediate wall 116 to an outermost position which is approximately radially adjacent to the inner terminal end of the internal threads 114. The hollow sleeve 118 is located concentrically about an axis of the receptacle 112 (FIGS. 4, 9–11). Because the hollow sleeve 118 has an outside diameter which is less than the inside diameter of the receptacle 112 at positions radially adjacent to the hollow sleeve 118, the space between the outside of the hollow sleeve 118 and the inside of the receptacle housing 102 defines an annular slot 124. The inner end of the annular slot 124 terminates at the intermediate wall 116. The annular slot 124 is also concentric with the axis of the receptacle 112. The annular slot 124 receives the forward non-threaded portion of the larger cylindrical end portion 56 of the sleeve member 52 of the male mating piece 38 when the external threads 70 of the male mating piece 38 (FIGS. 5 and 6) engage and mesh with the internal threads 114 of the receptacle 112 (FIG. 13).

Figure 9:
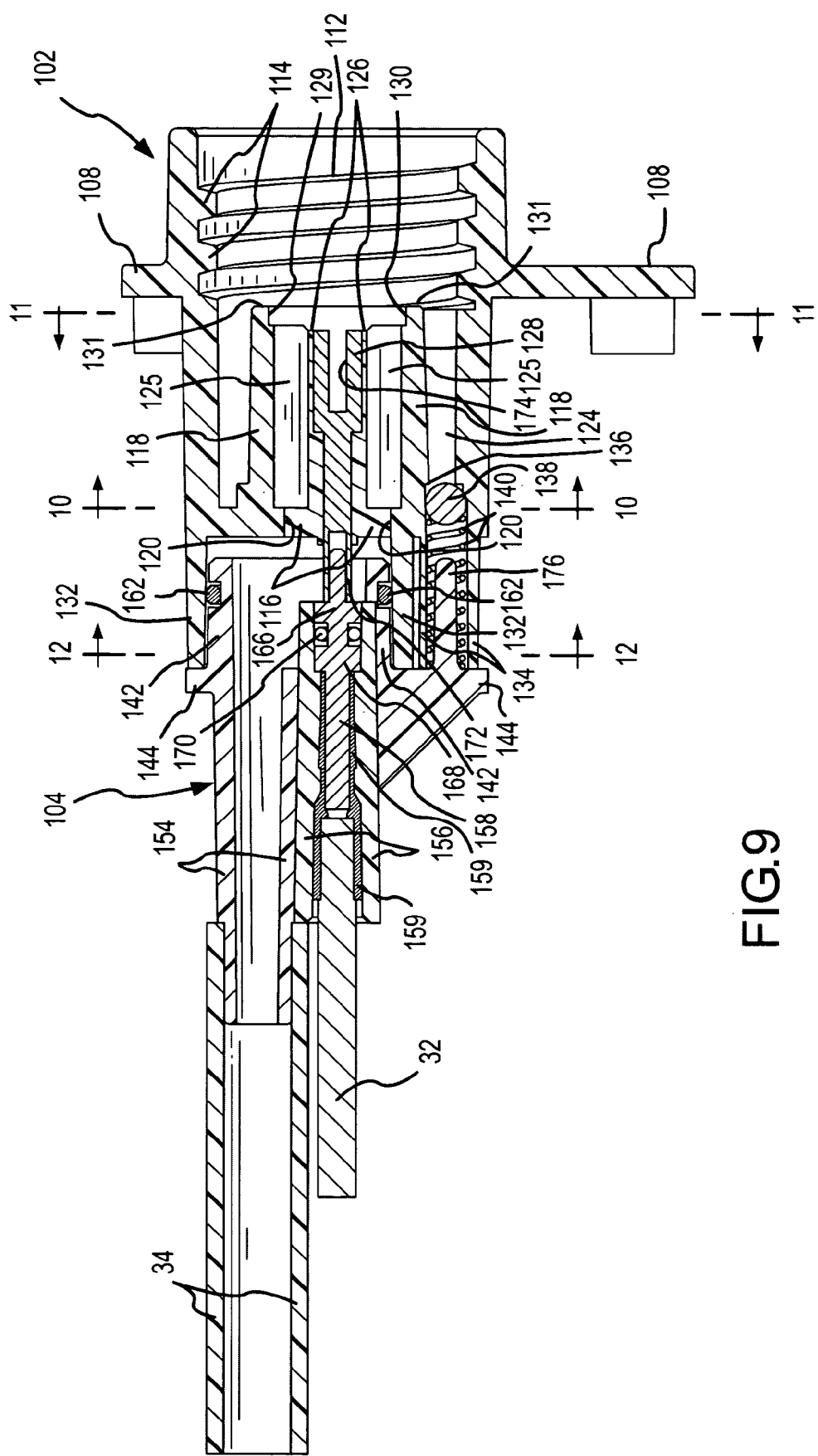
FIG. 9 is an axial cross-sectional view of the female mating piece of the accessory connector shown in FIGS. 1-4, taken substantially in the plane of line 9-9 in FIG. 2.
Figure 11:
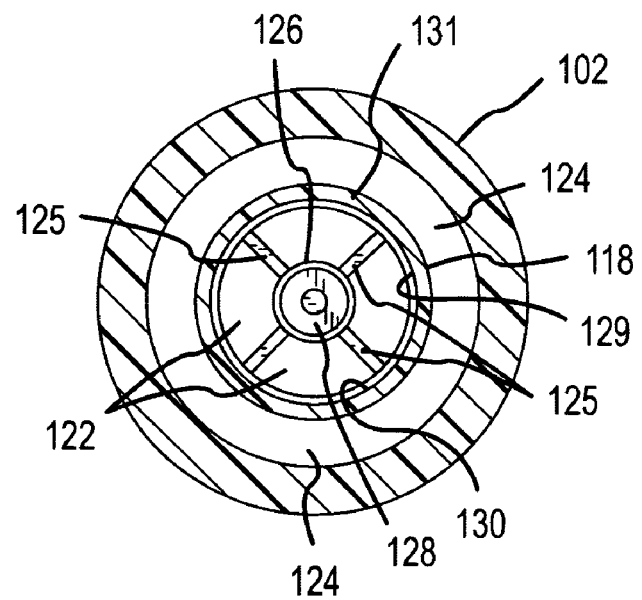
FIG. 11 is a transverse cross-sectional view taken substantially in the plane of line 11-11 of FIG. 9.

Ribs 125 extend radially inward from the hollow sleeve 118 within its hollow interior 122 to a hollow tube-like socket holder 126, as shown in FIGS. 4, 9 and 11. The ribs 125 position a socket holder 126 concentrically with the hollow sleeve 118 and concentrically about the axis of the receptacle 112. The socket holder 126 receives and holds an electrical socket 128. The electrical socket 128 transfers the RF energy from the supply connector 32 (FIG. 1) to the forward end 98 of the connector electrode 92 of the male mating piece 38 (FIG. 13). The ribs 125 are spaced at approximately equal circumferential intervals (FIG. 11) to permit the gas to flow between them from the opening 120 in the intermediate wall 116 through the interior 122 of the hollow sleeve 118.

Figure 14:
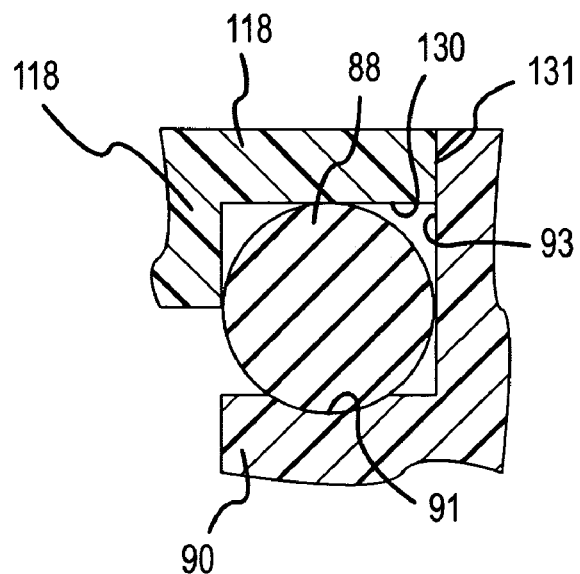
FIG. 14 is an enlarged partial view of FIG. 13 illustrating a gas-tight seal created by an O-ring located between the connected female and male mating pieces shown in FIG. 13.

An outer end of the hollow sleeve 118 includes an interior recess 129 which extends generally concentrically with the axis of the receptacle 112. The recess 129 includes a cylindrical sidewall 130 which faces radially inward. The outside surface of the O-ring 88, which is attached to the forward sleeve-like extension 90 of the spool-like body portion 76, contacts the cylindrical surface 130 of the recess 129 when the male mating piece 38 is connected to the female mating piece 36 (FIGS. 13 and 14). The O-ring 88 is slightly compressed in a radial direction, between the sleeve like extension 90 and the cylindrical sidewall 130, thereby establishing a radial seal between the sleeve 118 of the female mating piece 36 and the forward end of the spool-like body portion 76 of the male mating piece 38 (FIGS. 13 and 14). The radial seal, established by compression of the O-ring 88 between the extension 90 and the inside cylindrical sidewall 130, confines the gas to flow from the interior 122 of the hollow sleeve 118 into the gas passageway 86 of the spool-like body portion 76 (FIG. 13). The gas seal from the radially compressed O-ring 88 remains effective even though the mating pieces 36 and 38 may not be fully tightened in their connected relationship. The outer end of the hollow sleeve 118 also includes a outer edge contact surface 131, which extends radially outward with respect to an axis through the hollow sleeve 118. The outer edge contact surface 131 contacts, or is positioned closely adjacent to, the surface 93 of the male mating piece 38, when the pieces 36 and 38 are connected (FIGS. 13 and 14).

Figure 12:
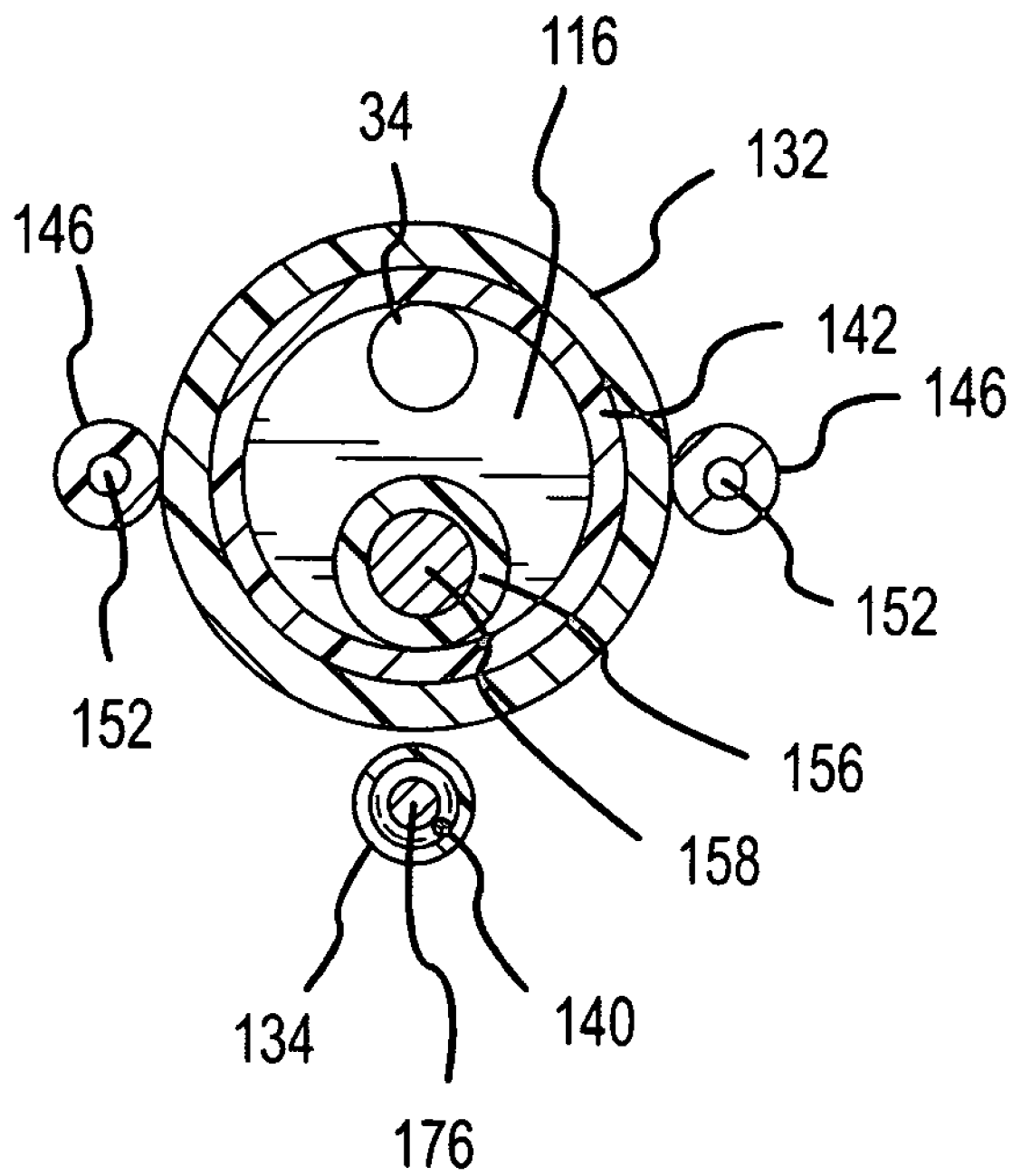
FIG. 12 is a transverse cross-sectional view taken substantially in the plane of line 12-12 of FIG. 9.
Figure 15:
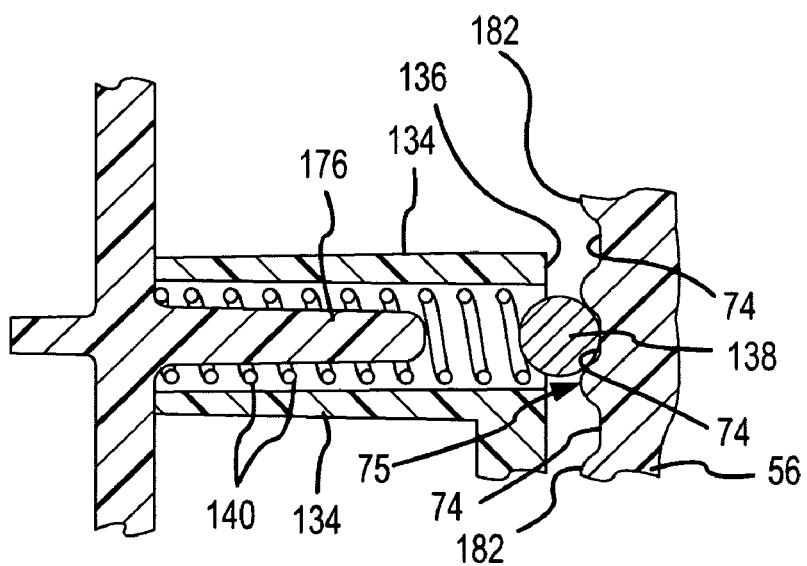
FIG. 15 is an enlarged cross-sectional view taken substantially in the plane outline 15-15 of FIG. 13.

At the inner end of the receptacle housing 102, a cylindrically-shaped socket 132 extends from the intermediate wall 116. The socket 132 extends inwardly away from the intermediate wall 116 on the opposite side from which the receptacle 112 extends outwardly away from the intermediate wall 116 (FIGS. 3 and 9). A tubular-shaped channel 134 extends inward from the intermediate wall 116 at a location outside of the socket 132 (FIGS. 3, 9 and 12). The channel 134 extends parallel to an axis of the receptacle 112 at a location which aligns axially with the annular slot 124. An outer end 136 of the channel 134 opens through the intermediate wall 116 and into the annular slot 124. A metal ball 138 is biased into the outer end 136 of the channel 134 by a coiled bias spring 140. The spring 140 is located inwardly behind the metal ball 138 and biases the metal ball outwardly within the channel 134. The outwardly biased ball 138 contacts and fits within one of the detents 74 formed in the forwardmost edge 75 of the larger cylindrical end portion 56 of the sleeve member 52, when the mating pieces 36 and 38 are connected (FIGS. 13 and 15). The ball 138, biased by the spring 140 into a detent 74, prevents accidental and unintentional unscrewing or disconnecting of the male mating piece 38 from the female mating piece 36 in a manner described more completely below.

The tailpiece 104 includes an outward-extending cylindrically-shaped sleeve 142. The cylindrically shaped sleeve 142 is received within the socket 132 of the housing receptacle 102 when the tailpiece 104 and the receptacle housing 102 are connected (FIG. 12). An attachment flange 144 of the tailpiece 104 extends outwardly from the sleeve 142 at a location adjacent to the inward extent of the sleeve 142. Two screw plugs 146 are located on the receptacle housing 102 at diametrically-opposite positions outside of the cylindrically-shaped socket 132. Holes 148 (FIGS. 3 and 12) are formed in the attachment flange 144 in alignment with the screw plugs 146, and the screws 106 extend through the holes 148 and connect with internally threaded openings 152 (FIG. 12) in the screw plugs 146 to connect the tailpiece 104 to the receptacle housing 102.

The tailpiece 104 includes a gas connection tube 154. The outer end of the gas connection tube 154 communicates with the interior of the sleeve 142. The inner end of the gas connection tube 154 is connected to the supply conduit 34 from the gas delivery apparatus 28 (FIG. 1). Gas flows through the gas connection tube 154 into the tailpiece 104 and into the female mating piece 36. The tailpiece 104 also includes an electrical connection tube 156. The electrical connection tube 156 is located concentrically with the axis through the receptacle 112. An electrical terminal 158 is located within the electrical connection tube 156, and the inner end of the electrical terminal 158 is received in a socket portion of a conventional female crimp-on connector terminal 159 which has been crimped onto the RF supply conductor 32. The electrical socket 128 is connected to the outer end of the electrical terminal 158. In this manner, RF energy from the electrosurgical generator 26 (FIG. 1) is conducted from the supply conductor 32 into the tailpiece 104 and the female mating piece 36.

The cylindrically-shaped sleeve 142 of the tailpiece 104 has an outer diameter slightly smaller than the inner diameter of the cylindrically-shaped socket 132. An annular groove 160 is formed around the sleeve 142 and an O-ring 162 is retained within the groove 160. When the sleeve 142 is inserted into the socket 132, the O-ring 162 creates a gas-tight seal between the inside cylindrical surface of the socket 132 and the outside cylindrical surface of the sleeve 142. A hollow interior chamber 164 is defined by the connected sleeve 142 and socket 132. The forward end of the gas connection tube 154 opens into the interior chamber 164, so that the gas flowing from the gas connection tube 154 enters and fills the interior chamber 164. The inner end of the hollow sleeve 118 also opens into the interior chamber 164, so that gas from the interior chamber 164 flows into the interior 122 of the sleeve 118.

The electrical terminal 158 includes first and second raised annular ridges 166 and 168 located between its inner and outer ends (FIGS. 3, 4 and 9). The ridges 166 and 168 support and locate an O-ring 170 at a middle location along the length of the electrical terminal 158. When the electrical terminal 158 is located in the electrical connection tube 156, the O-ring 170 creates a gas-tight seal between the inside surface of the electrical connection tube 156 and the electrical terminal 158, thereby preventing gas from leaking from the interior chamber 164 by flowing inwardly along the electrical terminal 158 and out of the inward end of the electrical connection tube 156.

The conventional crimped-on female terminal 159, after having been crimped on to the RF supply conductor 32, is inserted outwardly into the electrical connector tube 156 from the inner end of the tube 156. The tube 156 and the terminal 159 have appropriate geometry that allows the terminal 159 to snap into a retained position within the tube 156. The inner end of the electrical terminal 158, after having been connected to the electrical socket 128 and the O-ring 170, is then inserted inwardly into the connector tube 156 from the outer into the tube 156, to establish the electrical connection from the RF supply conductor 32 to the electrical socket 128.

An alignment prong 176 extends outwardly from the attachment flange 144, at a location to extend into the channel 134 when the receptacle housing 102 and the tailpiece 104 are connected (FIGS. 9, 13 and 15). The coiled spring 140 surrounds the alignment prong 176. The alignment prong 176 in conjunction with sleeve 142 orient the tailpiece 104 with the receptacle housing 102 for proper assembly, due to the nonconcentric position of the electrical socket 128 with respect to an axis through the socket 132 of the receptacle housing 102. The alignment prong 176 extends outwardly a sufficient distance within the channel 134 to avoid contacting the ball 138 when the ball makes contact with the forward edge 75 of the larger cylindrical end portion 56 of the sleeve member 52. In this manner, the ball 138 is resiliently biased outward only from the force of the coiled spring 140. The inside transverse dimension of the channel 134 and the outside transverse dimension of the alignment prong 176 allow the coils of the spring 140 to flex freely without adversely diminishing the bias force from the spring 140.

Details of the connection relationship of the female and male mating pieces 36 and 38 of the connector 20 are shown generally in FIGS. 13-15. The connected-together relationship occurs when the larger cylindrical end portion 56 of the sleeve member 52 is screwed into the receptacle 112 of the receptacle housing 102, until the forward edge 75 of larger cylindrical end portion 56 of the sleeve member 52 is at an inwardmost location within the annular slot 124 which abuts the intermediate wall 116. The smaller cylindrical end portion 58 is gripped and rotated to engage and mesh the external threads 70 of the sleeve member 52 with the internal threads 114 of the receptacle 112, thereby advancing the sleeve member 52 forwardly and into the receptacle 112. The forward movement of the sleeve member 52 causes the contact surface 72 of the abutment shoulder 66 to push against the rear-facing contact surface 82 of the rear annular ridge 80 of the spool-like body portion 76, thereby moving the hub member 54 forward and into the receptacle 112.

The forward movement of the hub member 54 pushes the forward end 98 of the connector electrode 92 into the hollow outer end 174 of the electrical socket 128. With the forward end 98 of the connector electrode 92 inserted within the hollow outer end 174 of the electrical socket 128, a continuous electrical connection is established between the electrosurgical generator 26 and the electrode (not shown) within the nozzle 46 of the accessory 22 (FIG. 1). Electrical energy generated by the electrosurgical generator is conducted through the RF supply conductor 32 to the electrical terminal 158 and the connected electrical socket 128 of the female mating piece 36. The connector electrode 92 of the male mating piece 38 receives the electrical energy from the electrical socket 128 and transfers it through the accessory conductor 48 to the electrode (not shown) within the nozzle 46 of the handpiece 42 (FIG. 1).

The forward movement of the hub member 54 moves the O-ring 88 into the recess 129 in the outer end of the hollow sleeve 118. The O-ring 88 is compressed between the cylindrical sidewall 130 of the recess 129 and the sleeve-like extension 90 of the spool-like body portion 76 of the hub member 54 (FIG. 14). In this compressed state, the gas seal O-ring 88 confines the gas flowing from the interior 122 of the hollow sleeve 118 into the gas passageway 86 of the hub member 54. The gas from the gas delivery apparatus 28 flows through the supply conduit 34 to and through the gas connection tube 154, the interior chamber 164, and into the interior 122 of the sleeve 118 of the female mating piece 36. Because of the gas seal obtained by the O-ring 88, the entire amount of gas flow is transferred from the interior 122 of the sleeve 118 into the gas passageway 86 of the spool-like portion 76 and into the stub portion 84 of the male mating piece 38. The gas flows from the stub portion 84 and into the accessory hose 44 to the nozzle 46 of the handpiece 42 (FIG. 1).

Establishing the gas-tight seal does not depend upon the male mating piece 38 being screwed into the female mating piece 36 to the maximum extent possible. Instead, the seal created by the O-ring 88 remains gas tight so long as the O-ring 38 is compressed against the cylindrical sidewall 130, as shown in FIGS. 13 and 14. The O-ring 88 maintains the gas-tight seal through the accessory connector 20 even if the male mating portion 38 becomes slightly loosened from the female mating portion 36. A slight axial separation of the mating pieces does not destroy the gas-tight seal until enough axial movement has occurred to withdraw the O-ring 88 from contact with the cylindrical sidewall 130. Therefore, if the male mating piece 38 is bumped or otherwise loosened, the gas-tight seal will not necessarily be lost.

Figure 16:
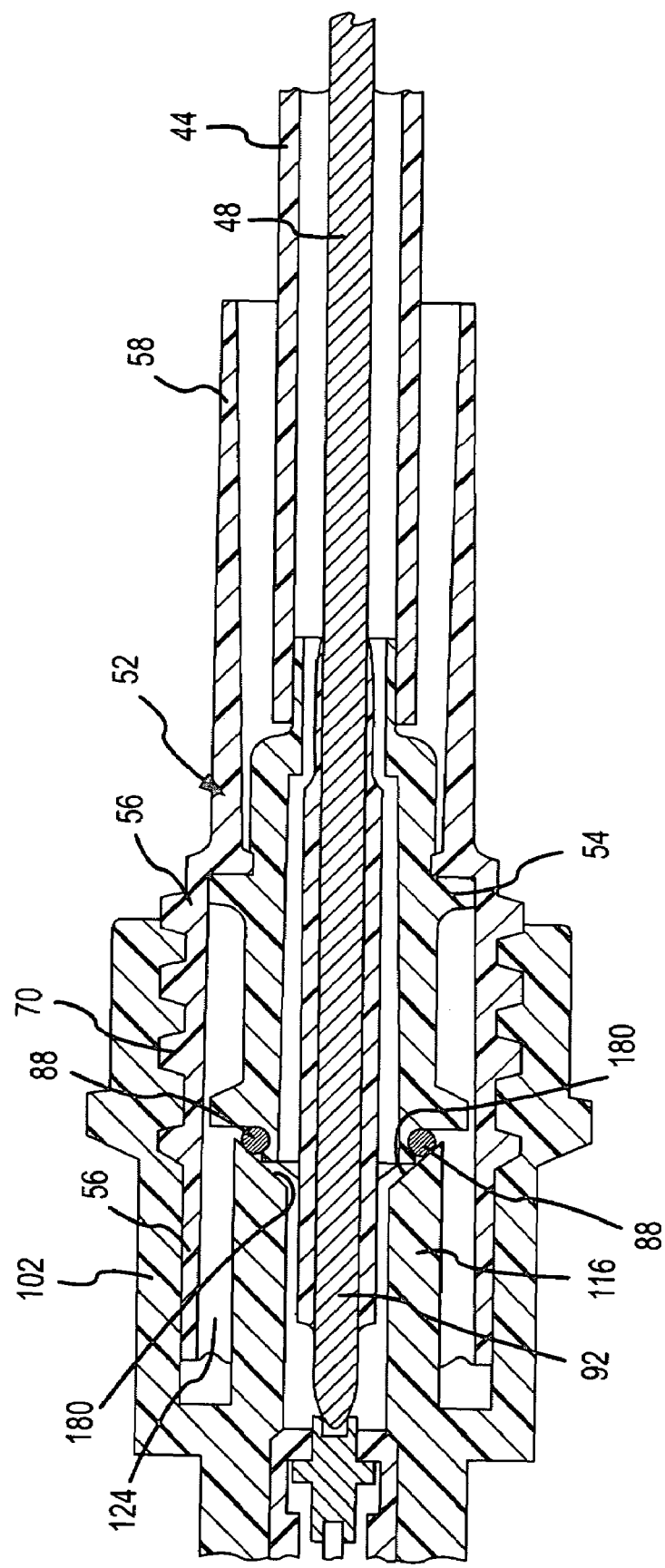
FIG. 16 is an cross sectional view, related to FIG. 13, of the male portion of the accessory connector shown in FIGS. 1-5, shown in a connected relationship with a prior art form of a female mating piece of a gas-assisted electrosurgical accessory connector.

Because the force created by the resilient compression of the O-ring 88 is radial, its resilient compression force does not push the mating pieces 36 and 38 away from one another to establish a leak, as is possible in the prior art form of the accessory connector shown in FIG. 16. Rather, the radial force from compression of the O-ring 88 frictionally helps to resist the separation of the mating pieces.

The ability to tolerate a slight amount of separation of the mating pieces 36 and 38 is contrasted to the prior art arrangement shown in FIG. 16. Instead of the cylindrical recess 129 which creates the cylindrical sidewall 130 (FIGS. 9, 13 and 14) to establish the radial compression seal, the prior art female mating piece 36' has a frustoconically shaped surface 180 located at the outer end of the hollow sleeve like member 118'. The O-ring 88 contacts the frustoconically shaped surface 180 principally in axial compression. Consequently, any slight loosening of the mating pieces, such as might result from the natural movement of the accessory during the surgical procedure or as a result of accidentally bumping or jostling the accessory, causes a slight axial separation of the O-ring 88 from the frustoconically shaped surface 180, thereby creating a gas leak. Consequently, the gas-tight seal can only be maintained so long as the mating pieces are completely and tightly connected. Since movement of the accessory 22 (FIG. 1) during the surgical procedure is persistent, thereby creating the possibility of slightly loosening the connection of the mating pieces, the radial seal established by the O-ring 88 within the recess 129 (FIGS. 9, 13 and 14) maintains the improved gas-tight seal.

In addition to maintaining an improved gas-tight seal, the accessory connector 20 inhibits unscrewing the mating pieces 36 and 38 by the use of the outward-biased metal ball 138 which interacts with the detents 74 formed on the forward edge 75 of the large cylindrical end portion 56 of the sleeve-like member 52, as shown in FIGS. 13 and 15. As the large cylindrical end portion 56 of the sleeve member 52 moves forward and inwardly into the receptacle 112, the forward edge 75 contacts the ball 138 at the outer end 136 of the channel 134. The forward edge 75 pushes the ball 138 inwardly against the biasing spring 140 due to the forward advancement of the sleeve member 52. After the sleeve member 56 has been screwed into the receptacle 112 to a certain extent, a forwardmost portion 182 of the forward edge 75 between the detents 74 begins contacting and transversing across the ball 138. The ball 138 moves from one forwardmost portion 182 into an adjoining detent 74, as the sleeve member 52 rotates. As the sleeve member 52 continues to advance forwardly, the spring 140 is compressed more by the forwardmost portions 182 of the front edge 75, and the ball 138 is biased more deeply into the detents 74. As the ball 138 is forced more deeply into each detents 74, more rotational force is required to push the ball 138 out of each detent 74 by rotating the sleeve member 52. The maximum forward advancement of the sleeve member 52 is limited by the surface 93 of the hub member 54 coming into contact with the surface 131 of the sleeve 118 as shown in FIGS. 13 and 14. The rotation of the sleeve member 52 stops when the ball 138 is pushed inwardly into a detent 74 by the bias force from the compressed spring 140.

The bias force from the spring 140 which pushes the ball 138 into a detent 74 creates resistance to the rotation of the sleeve member 52. To rotate the sleeve member 52 after the ball 138 has been positioned in a detent 74, the bias force from the spring 140 must be overcome by pushing the ball 138 inwardly so that the ball 138 moves out of the detent 74. The sleeve member 52 must be gripped and significant force applied to rotate it and overcome the bias force from the spring 140 to move the ball 138 out of the detent 74. The amount of force required is significant. The typical jostling and continued movement of the accessory hose 44 during the course of the surgical procedure is insufficient to create enough force to rotate the sleeve member 52 and push the ball 138 out of the detent 74 in opposition to the bias force from the spring 140. The opposition force from the bias spring 140 therefore prevents or substantially inhibits the sleeve member 52 of the male mating piece 38 from unintentionally loosening and unscrewing out of the receptacle 112 of the female mating piece 36.

The resistance created by the compressed bias spring 140 and the ball 138 assists in preventing the male mating piece from inadvertently unscrewing from the female mating piece. However, even if the male mating piece does unscrew slightly from the female mating piece, or is not completely tightened when the connection is initially established, the radial compression of the gas seal from the O-ring 88 still maintains a fluid tight seal. The resistance to unscrewing the male mating piece from the female mating piece can be overcome to disconnect the male mating piece 38 from the female mating piece by firmly gripping the smaller cylindrical end portion 58 of the sleeve member 52 and rotating the sleeve member 52. Thus, although the male mating piece is inhibited from unintentionally loosening, the inhibition is not so great as to prevent disconnecting the female and male mating portions. Other significant improvements will become apparent upon recognizing the significance of the present invention.

A presently preferred embodiment of the present invention and many of its improvements have been described with a degree of particularity. This description is a preferred example of implementing the invention, and is not necessarily intended to limit the scope of the invention. The scope of the invention is defined by the following claims.

What is claimed:

1. A gas-assisted electrosurgical accessory connector formed by two mating pieces connectable to one another with a relative connection movement along an axis toward one another, comprising:
    a sealing surface formed on one mating piece and extending generally parallel with the axis for a distance along the axis;
    a resilient radial sealing member carried on the other mating piece at a location which contacts and seals against the sealing surface with radial force upon the two mating pieces connecting with relative connection movement;
    a retention mechanism operative between the mating pieces when connected with relative connection movement, the retention mechanism restraining the connected mating pieces against separation from one another with movement away from one another along the axis, wherein the retention mechanism further comprises:
    a recess formed on one of the mating pieces; and
    a retention member carried on the other one of the mating pieces, the retention member moving into the recess upon the two mating pieces connecting with relative connection movement, the retention member moving out of the recess with manual force applied between the two connected mating pieces to separate the connected mating pieces from one another.

2. An accessory connector as defined in claim 1, wherein:
    the one of the mating pieces upon which the recess is formed includes a cylindrical end portion;
    the other one of the mating pieces upon which the retention member is carried comprises an annular slot into which the cylindrical end portion extends upon connection of the mating pieces with relative connection movement;
    the cylindrical end portion includes a detent formed therein;
    the recess includes the detent; and
    the biased retention member includes a ball positioned in the other one of the mating pieces at a position within the annular slot to contact and extend within the detent upon connection of the mating pieces with relative connection movement and to withdraw from within the detent upon separation of the mating pieces from one another.

3. An accessory connector as defined in claim 2, wherein the retention mechanism further comprises:
    a biasing member operative between the ball and the other one of the mating pieces to bias the ball into the detent upon connection of the mating pieces and to resist withdrawal of the ball from the detent upon separation of the mating pieces.

4. An accessory connector as defined in claim 3, wherein:
    the biasing member comprises a coil spring.

5. An accessory connector as defined in claim 3, wherein:
    the cylindrical end portion includes a forward facing cylindrical contact surface;
    a plurality of detents are formed and circumferentially spaced at locations in the forward facing contact surface;
    the one mating piece includes a channel having an outer end which opens into the annular slot;
    the ball is positioned within the channel; and
    the biasing member comprises a coil spring located within the channel to bias the ball into contact with the detents and the forward facing contact surface of the cylindrical end portion upon connection of the mating pieces with relative connection movement.

6. A gas-assisted electrosurgical accessory connector having a male mating piece and a female mating piece which interconnect together to conduct RF electrical energy and a gas flow from a gas-assisted electrosurgical unit to an electrosurgical accessory; the gas-assisted electrosurgical unit including an electrosurgical generator which generates RF electrical energy and a gas delivery apparatus which delivers the gas flow; the electrosurgical accessory including the male mating piece, an accessory hose, an accessory conductor, a nozzle connected to receive the gas flow from the accessory hose and to issue the gas flow as a flow stream, and an electrode positioned within the nozzle and connected to the accessory conductor to transfer the RF energy to ionize conductive pathways within the flow stream; the male mating piece including a gas passageway that is adapted to be fluidly connected to the accessory hose, the male mating piece also including a connector electrode, that is adapted to be electrically connected to the accessory conductor; the female mating piece including an electrical terminal that is adapted to receive the RF energy generated by the electrosurgical generator and to electrically contact the connector electrode of the male mating piece upon interconnection of the female and male mating pieces, the female mating piece also including an internal gas flow path that is adapted to receive the gas flow delivered from the gas delivery apparatus and to conduct the gas flow to the gas passageway of the male mating piece upon interconnection of the female and male mating pieces; the accessory connector further comprising:
    an annular and radially compressible gas seal member attached to the male mating piece and surrounding the gas passageway; and
    an outer wall attached to the female mating piece and surrounding the internal gas flow path, the outer wall defining a cylindrical recess therein, the cylindrical recess receiving the annular gas seal member in radial compression against the cylindrical recess to create a gas tight connection between the gas flow path and the gas passageway upon interconnection of the male and female mating pieces.

7. An accessory connector as defined in claim 6, wherein the female and male mating pieces include complementary threads which mesh with one another upon screwing the male mating piece into the female mating piece to interconnect the mating pieces, the accessory connector further comprising:
a retaining mechanism including a biasing element connected to one of the mating pieces to bias the male mating piece against unscrewing from the female mating piece.

8. An accessory connector as defined in claim 7, wherein:
the male mating piece has a forward edge;
the retaining mechanism includes a series of detents on the forward edge of the male mating piece;
the retaining mechanism includes a ball connected to the female mating piece at a location to fit within a detent upon interconnection of the female and male mating pieces; and
the biasing element comprises a spring connected to the ball to bias the ball into the detent upon interconnection of the female and male mating pieces to restrain the male mating piece against unscrewing from the female mating piece.

9. An accessory connector as defined in claim 6, wherein the gas seal member comprises an O-ring.

10. An accessory connector as defined in claim 9, wherein the male mating piece includes a hollow sleeve member and an interior hub member surrounded by the sleeve member and confined within the sleeve member, the sleeve member rotating relative to the hub member, the sleeve member including external threads, and the gas passageway extending through the hub member; the female mating piece including a receptacle housing which defines an interior receptacle with interior threads, the interior gas flow extending through the receptacle housing and into the receptacle; the male mating piece is interconnected to the female mating piece by screwing the threads of the sleeve member into the threads of the receptacle, and the gas passageway extends through the hub member, and wherein:
the O-ring is attached to the hub member.

11. An accessory connector as defined in claim 6, wherein the electrical terminal is at least partially within the gas flow path, the accessory connector further comprising:
a terminal seal connected around the electrical terminal to create a gas tight seal between the electrical terminal and the female mating piece to prevent gas from flowing from the gas flow path out of the female mating portion around the electrical terminal.

12. An accessory connector as defined in claim 6, further comprising:
a retention mechanism operative between the connected mating pieces to restrain the connected mating pieces against separation from one another by movement of the connected mating pieces away from one another.

13. A gas-assisted electrosurgical accessory connector formed by two mating pieces connectable to one another with a relative rotational connection movement along an axis toward one another, the accessory connector conducting a gas flow and RF electrical energy between the two mating pieces comprising:
a retention mechanism operative between the mating pieces when connected with relative connection movement, the retention mechanism restraining the connected mating pieces against rotation with respect to one another to separate from one another along the axis, wherein the retention mechanism comprises:
a recess formed on one of the mating pieces;
a retention member carried on the other one of the mating pieces, the retention member moving into the recess upon the two mating pieces connecting with relative connection movement, the retention member moving out of the recess from manual rotational force applied between the two mating pieces to separate the mating pieces from one another.

14. An accessory connector as defined in claim 13, wherein:
the one of the mating pieces upon which the recess is formed includes a cylindrical end portion;
the other one of the mating pieces upon which the retention mechanism is carried comprises an annular slot into which the cylindrical end portion extends upon connection of the mating pieces with relative connection movement;
the cylindrical end portion includes a detent formed therein;
the recess includes the detent; and
the retention member includes a ball positioned in the other one of the mating pieces at a position within the annular slot to contact and extend within the detent upon connection of the mating pieces with relative connection movement and to withdraw from within the detent upon separation of the mating pieces from one another.

15. An accessory connector as defined in claim 14, wherein the retention mechanism further comprises:
a biasing member contacting the ball to bias the ball into the detent upon connection of the mating pieces and to resist withdrawal of the ball from the detent upon separation of the mating pieces.

16. A method of connecting together two mating pieces of a gas-assisted electrosurgical accessory to a gas-assisted electrosurgical unit by interconnecting a male mating piece and a female mating piece to conduct RF electrical energy and a gas flow from the gas-assisted electrosurgical unit to the electrosurgical accessory; the gas-assisted electrosurgical unit generating the RF electrical energy and delivering the gas flow; the electrosurgical accessory including the male mating piece, an accessory hose, an accessory conductor, a nozzle connected to receive the gas flow from the accessory hose and to issue the gas flow as a flow stream, and an electrode positioned within the nozzle and connected to the accessory conductor to transfer the RF energy to ionize conductive pathways within the flow stream; the male mating piece including a gas passageway that is fluidly connected to the accessory hose, the male mating piece also including a connector electrode that is electrically connected to the accessory conductor; the female mating piece including an electrical terminal that is connected to receive the RF energy generated by the gas-assisted electrosurgical unit and to electrically contact the connector electrode of the male mating piece upon connection of the female and male mating pieces, the female mating piece also including an internal gas flow path that is connected to receive the gas flow delivered from the gas-assisted electrosurgical unit and to conduct the gas flow to the gas passageway of the male mating piece upon interconnection of the female and male mating pieces; said method comprising:
connecting the two mating pieces by moving the two mating pieces together along an axis in a relative axial connection movement;
contacting a sealing member carried on one mating piece with a sealing surface formed on the other mating piece, the sealing surface extending generally parallel with the axis for a distance along the axis; and resiliently compressing the sealing member in a radial direction relative to the axis in contact with the sealing surface to establish a gas tight seal over a range of relative axial connection movement extending from before the mating pieces achieve a fully connected relationship.

17. A method as defined in claim 16, further comprising:
conducting gas flow and RF electrical energy between the connected two mating pieces; and
contacting and sealing the sealing member with the sealing surface over a portion of the predetermined length of the sealing surface along the axis.

18. A method as defined in claim 17, further comprising:
conducting the gas flow and the RF electrical energy in a space circumscribed by the sealing surface and the contact of the sealing member with the sealing surface.

19. A method as defined in claim 16, wherein the sealing surface is generally cylindrically-shaped and concentric about the axis, and the sealing member is annularly shaped.

20. A method as defined in claim 16, further comprising:
restraining the connected mating pieces against separation from one another along the axis.

21. A method as defined in claim 20, further comprising:
restraining the connected mating pieces against separation by moving a retention member carried by one mating piece into a recess formed in the other mating piece upon the two mating pieces connecting with relative connection movement; and
moving the retention member out of the recess with manual force applied between two connected mating pieces to separate the mating pieces from one another.

22. A method as defined in claim 21, further comprising:
rotating the two mating pieces in one relative rotational direction with respect to one another to connect the mating pieces with relative connection movement; and
rotating the two mating pieces in the other relative rotational direction with respect to one another to separate the mating pieces.

23. A method as defined in claim 21, further comprising:
biasing a ball member into the recess upon connecting the two mating pieces with relative connection movement; and
overcoming a bias force biasing the ball member into the recess by manual force of rotating the two mating pieces in the other relative rotational direction to move the ball from the detent to permit separation of the mating pieces.

24. A method of connecting together and disconnecting two mating pieces of gas-assisted electrosurgical accessory in a connected together relationship, comprising:
connecting the two mating pieces by moving the two mating pieces together along an axis in a relative connection movement;
contacting a sealing member carried on one mating piece with a sealing surface formed on the other mating piece, the sealing surface extending generally parallel with the axis for a distance along the axis;
conducting a gas flow and RF electrical energy between the two connected mating pieces;
restraining the connected mating pieces against separation by moving a retention member carried by one mating piece into a recess formed in the other mating piece upon the two mating pieces connecting with relative connection movement; and
moving the retention member out of the recess with manual force applied between the two mating pieces to separate the mating pieces from one another.

25. A method as defined in claim 24, further comprising:
rotating the two mating pieces in one relative rotational direction with respect to one another to connect the mating pieces with relative connection movement;
biasing a ball member into the recess upon connecting the two mating pieces with relative connection movement;
rotating the two mating pieces in the other relative rotational direction with respect to one another to separate the mating pieces; and
overcoming a bias force biasing the ball member into the recess by manual force of rotating the two mating pieces in the other relative rotational direction to move the ball from the detent to permit separation of the mating pieces.

26. A method of connecting a gas-assisted electrosurgical accessory to a gas-assisted electrosurgical unit by interconnecting a male mating piece and a female mating piece to conduct RF electrical energy and a gas flow from the gas-assisted electrosurgical unit to the electrosurgical accessory; the gas-assisted electrosurgical unit generating the RF electrical energy and delivering the gas flow; the electrosurgical accessory including the male mating piece, an accessory hose, an accessory conductor, a nozzle connected to receive the gas flow from the accessory hose and to issue the gas flow as a flow stream, and an electrode positioned within the nozzle and connected to the accessory conductor to transfer the RF energy to ionize conductive pathways within the flow stream; the male mating piece including a gas passageway that is fluidly connected to the accessory hose, the male mating piece also including a connector electrode that is electrically connected to the accessory conductor; the female mating piece including an electrical terminal that is connected to receive the RF energy generated by the gas-assisted electrosurgical unit and to electrically contact the connector electrode of the male mating piece upon connection of the female and male mating pieces, the female mating piece also including an internal gas flow path that is connected to receive the gas flow delivered from the gas-assisted electrosurgical unit and to conduct the gas flow to the gas passageway of the male mating piece upon interconnection of the female and male mating pieces; said method comprising:
radially sealing the interconnected female and male mating pieces to create a gas-tight seal between the gas flow path and the gas passageway when the mating pieces are interconnected with one another.

27. A method as defined in claim 26, wherein the female mating piece includes an outer wall that defines a cylindrical recess, and the male mating piece includes a radially compressible gas seal that surrounds the gas passageway, further comprising:
inserting part of the male mating piece and the gas seal into the cylindrical recess to establish a radial seal between the mating pieces by radially compressing the gas seal between the male mating piece and the cylindrical recess.

28. A method as defined in claim 27, further comprising:
connecting the two mating pieces by moving the two mating pieces together along an axis in a relative axial connection movement; and wherein:
the cylindrical recess defines a sealing surface which extends parallel to the axis over a predetermined length; and
the predetermined length of the sealing surface permits the gas seal to contact and seal against the sealing surface over the range of relative connection movement approximately equal to the predetermined length of the sealing surface along the axis.

29. A method as defined in claim 27, wherein:
the gas passageway and the internal gas flow path are circumscribed by the sealing surface and the contact of the gas seal with the sealing surface; and
the connector electrode and the electrical terminal are circumscribed by the sealing surface and the contact of the gas seal with the sealing surface.

30. A method as defined in claim 27, wherein:
the gas seal is annularly shaped.

31. A method as defined in claim 27, wherein:
the gas seal comprises a resilient O-ring.

32. A method as defined in claim 27, wherein:
the male mating piece includes an extension which extends concentrically about the axis;
the O-ring is retained on the extension; and
the O-ring compresses substantially only radially between the extension and the sealing surface.

33. A method as defined in claim 27, wherein:
the sealing surface extends concentrically along the axis over a predetermined length; and
the predetermined length of the sealing surface permits the O-ring to contact, move along and seal against the sealing surface over a range of relative connection movement approximately equal to the predetermined length of the sealing surface when the mating pieces connect with relative connection movement.

34. A method as defined in claim 27, wherein:
the extension is hollow;
the gas moves through the hollow extension; and
at least one of the electrical terminal or connector electrode extends through the hollow extension.

35. A method as defined in claim 26, wherein the female and male mating pieces each include threads which are meshed together when the mating pieces are interconnected by screwing the male mating piece into the female mating piece, one mating piece including a recess and the other mating piece including a restraining member biased into contact with the recess upon interconnecting the mating pieces, the method further comprising:
biasing the male mating piece against unscrewing from the female mating piece by contacting the restraining member with the recess and biasing the restraining member within the recess to resist relative unscrewing movement of the male mating piece from the female mating piece.

* * * * *